US00PP29116P2

(12) United States Plant Patent
Delabroye

(10) Patent No.: US PP29,116 P2
(45) Date of Patent: Mar. 13, 2018

(54) ***HEUCHERA* PLANT NAMED 'MAGMA'**

(50) Latin Name: ***Heuchera* hybrid**
Varietal Denomination: Magma

(71) Applicant: Thierry Delabroye, Hantay (FR)

(72) Inventor: Thierry Delabroye, Hantay (FR)

(73) Assignee: Sandrine Delabroye, Hantay (FR)

( * ) Notice: Subject to any disclaimer, the term of this patent is extended or adjusted under 35 U.S.C. 154(b) by 8 days.

(21) Appl. No.: 14/999,540

(22) Filed: May 20, 2016

(51) Int. Cl.
*A01H 5/12* (2006.01)

(52) U.S. Cl.
USPC ..... Plt./440

(58) Field of Classification Search
USPC ..... Plt./440

CPC . A01H 5/02; A01H 5/025; A01H 5/00; A01H 5/12
See application file for complete search history.

(56) References Cited

PUBLICATIONS

BBV 334 2015 CNB New Plants *Heuchera* 'Magma' striking red, retrieved on Jul. 17, 2017, retrieved from the Internet at <http://www.bloembollenvisie.nl/Archive/bbv334/files/assets/basic-html/page29.html> p. 29.*
English translation of BBV 334 on Jul. 17, 2017, one page.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Magma' that is characterized by its unique conspicuous leaves that are red in color, its leaves that are very large in size and its vigorous and healthy growth habit.

2 Drawing Sheets

Botanical classification: *Heuchera* hybrid.
Cultivar designation: 'Magma'.

CROSS REFERENCE TO RELATED APPLICATIONS

This application is co-pending with a U.S. Plant Patent Applications filed for a plant derived from the same breeding program that are entitled *Heuchera* Plant Named 'Carmencita' (U.S. Plant Pat. No. 28,431).

BACKGROUND OF THE INVENTION

The present invention relates to a new and distinct cultivar of *Heuchera* of hybrid origin, botanically known as a *Heuchera* and is hereinafter referred to by its cultivar name 'Magma'.

The new cultivar was discovered by the Inventor in Hantay, France, as a chance seedling amongst many different *Heuchera* varieties in a trial plot in April of 2013. The trial plot contained hundreds of cultivars and proprietary seedlings of *Heuchera* from the Inventor's breeding program. The parentage of 'Magma' is therefore unknown. The objectives of the breeding program were to select cultivars that were floriferous with distinct foliage coloration.

Asexual propagation of the new cultivar was first accomplished under direction of the Inventor by tissue culture initiated from meristem tissue in Rijswijk, The Netherlands in June of 2015. Asexual propagation of the new cultivar by division and tissue culture has shown that the unique features are stable and reproduced true to type in successive generations

SUMMARY OF THE INVENTION

The following traits have been repeatedly observed and represent the characteristics of the new cultivar. These attributes in combination distinguish 'Magma' as a new and unique cultivar of *Heuchera*.

1. 'Magma' exhibits unique conspicuous leaves that are red in color.
2. 'Magma' exhibits leaves that are very large in size.
3. 'Magma' exhibits a vigorous and healthy growth habit.

'Magma' can be most closely compared to the cultivars 'Carmencita' and 'Beaujolais' (U.S. Plant Pat. No. 19,577). 'Carmencita' is similar to 'Magma' in spring leaf coloration. 'Carmencita' differs from 'Magma' in having a less vigorous plant habit, in having foliage that is redder in color in the summer and in having leaves that are smaller in size. 'Beaujolais' is similar to 'Magma' in leaf size and flowering habit. 'Beaujolais' differs from 'Magma' in having less intense and less red foliage coloration and in having flowers that are less white in color.

BRIEF DESCRIPTION OF THE DRAWINGS

The accompanying colored photographs illustrate the overall appearance and distinct characteristics of the new *Heuchera*. The photographs were taken of a plant two years in age as grown outdoors in a 15-liter container in Boskoop, The Netherlands.

The photograph in FIG. 1 provides a side view of the plant habit of 'Magma' in bloom.

Figure 1:
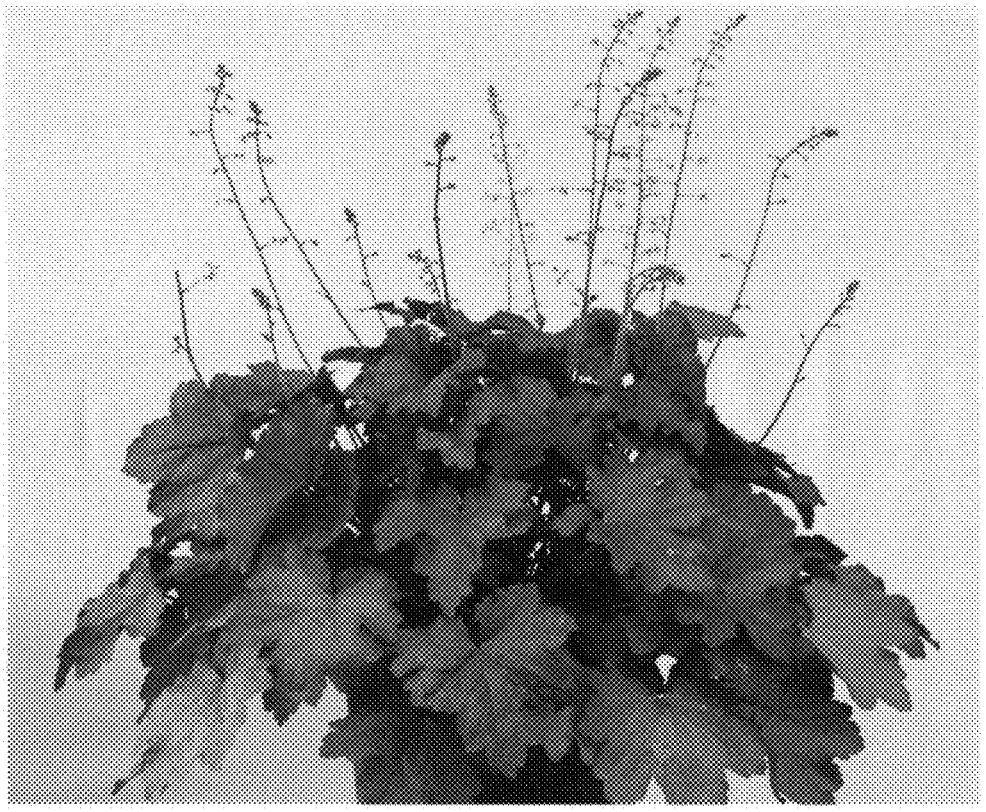
Figure 2:
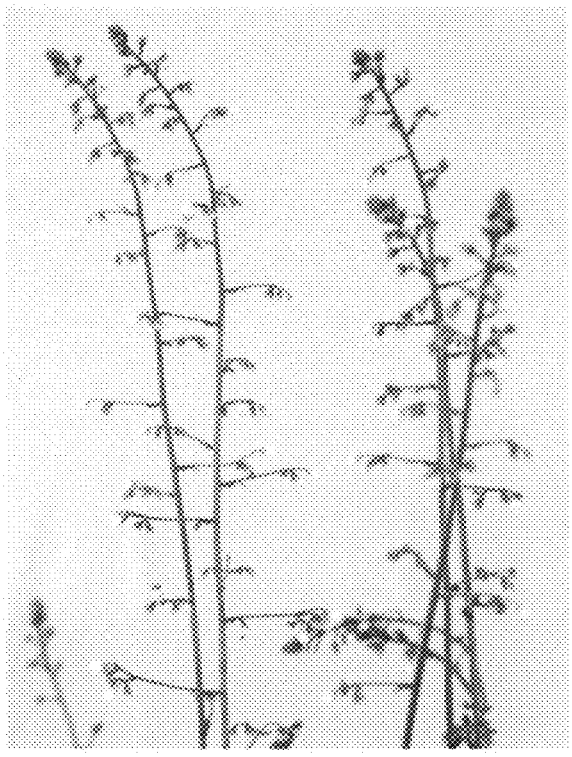

The photograph in FIG. 2 provides a close-up view of the inflorescences of 'Magma'.

Figure 3:
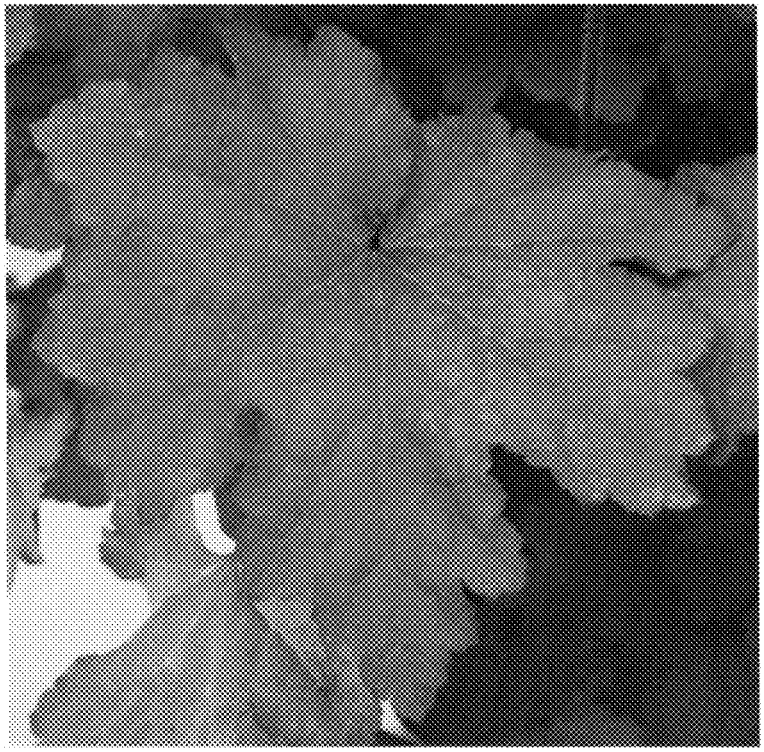

The photograph in FIG. 3 provides a close-up view of a leaf of 'Magma'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 2 year old plants of the new cultivar as grown outdoors in 15-liter containers in Hantay, France. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Early spring to early summer in The Netherlands.

*Plant type*.—Herbaceous perennial.

*Plant habit*.—Clump-forming, mounded foliage.

*Height and spread*.—Average of 37.5 cm in height from soil to top of leaves, 63.2 cm from soil to top of inflorescences, and an average of 77 cm in width.

*Hardiness*.—U.S.D.A. Zones 3 to 9.

*Diseases and pests*.—Not more susceptible to pests and diseases than other *Heuchera* varieties.

*Environmental stresses*.—Good sun tolerance with very little to no scorching observed.

*Root description*.—Fibrous roots on woody rootstalks, 163B in color.

*Branching habit*.—Basal rosette, with flowering stems arising from rosettes.

*Propagation*.—In vitro propagation is the preferred method, division are also possible.

*Growth rate*.—Vigorous.

Stem description (peduncle, flowering stem):

*Shape*.—Round.

*Stem color*.—N186D.

*Stem size*.—An average of 1 mm in diameter and 59.9 cm in length.

*Stem strength*.—Moderately strong.

*Stem aspect*.—Flowering stems grow in an average angle of 70° to base (0°=horizontal).

*Stem surface*.—Glabrous, densely covered with short soft hairs, average of 1.5 mm in length, NN155D in color.

*Stem number*.—Average of 15 flowering stems.

Foliage description:

*Leaf shape*.—Broad ovate to orbicular.

*Leaf division*.—Simple.

*Leaf base*.—Hastate, touching to slightly overlapping.

*Leaf apex*.—Obtuse, outer tip very short, mucronate.

*Leaf venation*.—Laciniate, upper veins; 184B to 184C, lower veins; 187C to 187D.

*Leaf margins*.—Lobed with an average of 7 lobes per leaf, lobe margins crenate.

*Leaf attachment*.—Petiolate.

*Leaf arrangement*.—Alternate, basal rosettes.

*Leaf orientation*.—Typically nearly horizontal to slightly hanging.

*Leaf surface*.—Both surfaces moderately glossy and sparsely to moderately covered with short strigose pubescence on main veins and secondary veins, hairs; an average of 0.05 mm in length and NN155D in color.

*Leaf color*.—Spring and young leaves; upper surface a color between 184A and 185A, lower surface a color between 185A and 187C, mature leaves in summer; upper surface; 183C, lower surface; 187C, older leaves and in fall; 183A and tinged 200B, winter color is not unique.

*Leaf size*.—Average of 16.4 cm in length and 16.8 cm in width.

*Leaf quantity*.—16 per basal rosette.

*Petioles*.—Round in shape, average of 25.7 cm in length and 4 mm in diameter, color is 187C, surface densely covered with very short strigose hairs; an average of 0.2 mm in length and 187C in color.

*Stipules*.—Small leafy stipules at the base of each leaf, narrow acute apex, an average of 2 cm in length and 7 mm in width and 187D in color, both surfaces glabrous.

Flower description:

*Inflorescence type*.—Numerous small bell-shaped flowers arranged on pyramidal panicles on flower scapes emerging from the base of the rosette.

*Inflorescence size*.—An average of 29.7 cm in height (excluding peduncle) and about 8 cm in width.

*Flower fragrance*.—None.

*Flower quantity*.—Average of 230 flowers per flowering stem.

*Flower lastingness*.—Average of one week.

*Flower buds*.—Elliptic in shape, an average of 4 mm in diameter and 2 mm in diameter, upper half a color between 155A and 158D, basal half 186B to 186C in color, surface is pubescent on calyx portion and glabrous on petal portion.

*Flower aspect*.—Outward to slightly nodding.

*Flower type*.—Campanulate.

*Flower size*.—About 6 mm in depth (height) and 3.5 mm in diameter.

*Petals*.—Average of 5, rotate arrangement and implanted in the hypanthium at base, oblanceolate in shape, margin is entire, apex is acute, upper and lower surface is glabrous and matte, color of upper and lower surface when opening and mature is NN155D, average of 3 mm in length and 1 mm in width.

*Calyx*.—Campanulate, sepals fused to hypanthium, 5 mm in length and 3 mm in diameter.

*Sepals*.—5, fused, campanulate hypanthium, oblong in shape, 5 mm in length and 1.5 mm in width, margin is entire, apex is obtuse, fused base, both surfaces are dull and moderately covered with very short glandular hairs about 0.2 mm in length and match the surface in color, color: immature and mature upper surface; color between 155A and 158D with top tinged 150D, immature and mature lower surface; color between 155A and 158D with lower half 186B to 186C.

*Pedicels*.—Average of 4 mm in length and 0.5 mm in width, moderate in strength, color 185A, average angle of 50° (0°=horizontal), surface is glabrous.

Reproductive organs:

*Gynoecium*.—Pistils; 2, about 3 mm in length, stigmas; pointed in shape and NN155D in color, styles; average of 2.75 mm in length and NN155D in color, ovaries; between N155A and 186D in color.

*Androecium*.—Stamens; 5, anthers; ovate in shape, 0.4 mm in length and 24B in color, filaments; 3 mm in length and NN155D in color, pollen is low in quantity and 21B to 21C in color.

*Seed/fruit*.—No fruit or seeds observed to date.

It is claimed:

1. A new and distinct cultivar of hybrid *Heuchera* plant named 'Magma' as herein illustrated and described.

* * * * *